United States Patent [19]
Luck et al.

[11] Patent Number: 6,074,689
[45] Date of Patent: Jun. 13, 2000

[54] COLONIC DELIVERY OF PROTEIN OR PEPTIDE COMPOSITIONS

[75] Inventors: Michael S. Luck, Cape Elizabeth; Joseph H. Crabb, Newfield, both of Me.

[73] Assignee: ImmuCell Corporation, Portland, Me.

[21] Appl. No.: 09/037,647

[22] Filed: Mar. 10, 1998

[51] Int. Cl.[7] .............................. A61K 9/16; A61K 39/40; B01J 2/30
[52] U.S. Cl. ..................... 427/2.21; 424/408; 424/490; 424/494; 424/497; 424/499
[58] Field of Search .................... 424/490, 497, 424/499, 408, 494; 427/2.14, 2.21

[56] References Cited

U.S. PATENT DOCUMENTS

| | | |
|---|---|---|
| 4,391,797 | 7/1983 | Folkman et al. .......................... 424/425 |
| 4,489,026 | 12/1984 | Yalkowsky ................................ 264/123 |
| 4,975,284 | 12/1990 | Stead et al. . | |
| 5,378,462 | 1/1995 | Boedecker et al. ................... 424/94.21 |
| 5,399,357 | 3/1995 | Akiyama et al. ......................... 424/457 |
| 5,536,507 | 7/1996 | Abramowitz et al. ................... 424/479 |
| 5,601,823 | 2/1997 | Williams et al. . | |
| 5,750,104 | 5/1998 | Sipos .................................... 424/94.21 |
| 5,958,452 | 9/1999 | Oshlack et al. .......................... 424/457 |
| 5,965,161 | 10/1999 | Oshlack et al. .......................... 424/457 |
| 5,993,806 | 11/1999 | Galle ....................................... 424/94.3 |

OTHER PUBLICATIONS

Roos et al., *J. of Nutrition* 125: 1238–1244 (1995).
Brüssow et al., *J. Clin. Microbiol.* 25: 982–986 (1987).
Tzipori et al., *Clin. Diag. Lab. Immunol.* 1: 450–463 (1994).
Davis et al., *Int. J. Pharm.* 21: 167–177 (1984).
Bartlett, J.F., *Clin. Infec. Dis.* 18 (Suppl. 4): S265–272 (1994).
Bartlett, J.G., *Gastroenterology* 89: 1192–1195 (1985).
Kreutzer & Milligan, *Johns Hopkins Med. J.* 143: 67–72 (1978).
McFarland et al., *JAMA* 271: 1913–1918 (1994).
Leung et al., *J. Pediatr.* 118: 633–637 (1991).
Lyerly et al., *Infec. Immun.* 59: 2215–2218 (1991).

*Primary Examiner*—Robert H. Harrison
*Attorney, Agent, or Firm*—Kevin M. Farrell

[57] ABSTRACT

Disclosed is a method for delivering an active protein or peptide to the colon. The steps of the method include providing a multiparticulate dosage core particle comprising 3 components, the total weight of the 3 components in dry form defining a batch size. The multiparticulate core particle is produced by the method comprising: a) providing an aqueous PEG solution, the dry weight of the PEG component representing from about 2.5% to about 15% of the batch size (weight/weight), the water component of the aqueous PEG solution representing approximately 30–60% of the batch size (weight/weight); b) providing a homogenous mixture of the active protein or peptide and microcrystalline cellulose, both in dry form, the active protein or peptide comprising from about 50% to about 95% of the batch size (weight/weight) and the microcrystalline cellulose comprising from about 2.5% to about 35% of the batch size (weight/weight); c) while mixing the components of step b), contacting the components of step b) with the aqueous PEG solution of step a), said contact being established by introducing the aqueous PEG solution as an atomized spray to the mixing components of step b); d) extruding the composition formed in step c); e) spheronizing the extruded composition of step d); f) drying the spheronized composition of step e) to a moisture level of less than about 7%; and g) screening the dried composition of step f) and collecting multiparticulate core particles. An outer enteric coating is then applied to the multiparticulate core particles to form coated multiparticulate particles. The coated multiparticulate particles are then administered orally to an individual. Also disclosed is a composition for delivering an active protein or peptide to the colon, the composition being produced by the method described in the preceding paragraph. In preferred embodiments, the active protein to be delivered is an immunoglobulin.

10 Claims, 5 Drawing Sheets

COLONIC DELIVERY OF PROTEIN OR PEPTIDE COMPOSITIONS

BACKGROUND OF THE INVENTION

Stability problems are known to be associated with the therapeutic oral administration of a protein (e.g., an antibody) or peptide intended to exert its therapeutic influence after passage through the stomach. More specifically, proteins or peptides tend to be degraded, or rendered therapeutically inactive, by the harsh environment of the gastrointestinal tract. The stomach is a characteristically low pH environment and the small intestine and colon contain a variety of gastric and intestinal proteases.

Hyperimmune bovine colostrum immunoglobulin (HBCIg) has been reported to be particularly resistant to gastrointestinal destruction, relative to other Igs. Early studies involving the administration of HBCIg for other gastrointestinal infections cited remarkable resistance to proteolytic digestion in the intestine of a heterologous host (Brussow et al., *J. Clin. Microbiol.* 25: 982–986 (1987)). Indeed there is evidence that bovine IgG1 is more resistant to proteolysis by trypsin, chymotrypsin and pepsin than other Igs (Butler, *Vet. Immun. and Immunol. Pathology* 4: 43–152 (1983); McClead and Gregory, *Inf. and Immun.* 44: 474–478 (1984)). Approximately 20% of immunoreactive bovine colostral Ig (as measured by radial immunodiffusion) was detectable in the ileal samples of human volunteers who consumed about 5 g of a $^{15}$N-labeled bovine colostral Ig preparation after fasting (Roos et al., *J. of Nutrition* 125: 1238–1244 (1995)). This recovery was cited as evidence of significant gastrointestinal resistance by comparison to the normal ileal digestibility of other milk proteins reported in the literature to be 90% or more. Unfortunately, the 20% immunoreactive Igs detected in this study were not shown to be functional (i.e., antigen binding).

Bovine Igs have also been cited as being particularly resistant to stomach acid (Rump et al., *Clin. Invest.* 70: 588–594 (1992)). Unfortunately, this assertion was based on exposure to "artificial gastric juice" (pH 2.4–4.0) for 24 hours. However, natural gastric juice is considered to have a pH of 1–2 (Kutchai, Gastrointestinal Systems, in Physiology 2nd ed: Berne and Levy (eds); 649–718; Mosby (St. Louis, Mo.) (1988)), not 2.4–4.0. Indeed, exposure of HBCIg to artificial gastric juice of pH 2.0 results in irreversible denaturation of antigen binding activity. Further, in studies of gnotobiotic piglets, even after pretreatment of the animals with cimetidine (which raised the mean gastric pH to 3.13), only 0.2–9% of the total activity of HBCIg was recovered in the stool (Tzipori et al., *Clin. Diag. Lab. Immunol.* 1: 450–463 (1994)). These data indicate that the majority of antibody activity is destroyed during passage through the gastrointestinal tract even with modified gastric pH, and that issues of formulation must be addressed to improve the proportion of active antibodies delivered via the oral route. The development of dosage formulations for oral immunotherapy must meet criteria of gastric resistance followed by complete release at the site of action (e.g., small intestine or colon).

The transit time of orally administered antibody varies considerably, and is dependent on the individual subject's physiology, fed or fasted status, type of food ingested, etc. In the fasted state, antibodies have a transit time through the small intestine of the order of 1–2 hours (Roos et al., *J. of Nutrition* 125: 1238–1244 (1995)). In contrast, systemic administration of antibodies would be expected to have a much longer duration of activity, as IgA has a half-life in circulation of about 6 days. Therefore, for sustained duration of activity, oral antibody therapy requires several doses per day, whereas systemic or injectable antibody therapy would require doses of the order of once per week.

SUMMARY OF THE INVENTION

The present invention relates, in one aspect, to a method for delivering an active protein or peptide to the colon. The steps of the method include providing a multiparticulate dosage core particle comprising 3 components, the total weight of the 3 components in dry form defining a batch size. The multiparticulate core particle is produced by the method comprising: a) providing an aqueous PEG solution, the dry weight of the PEG component representing from about 2.5% to about 15% of the batch size (weight/weight), the water component of the aqueous PEG solution representing approximately 30–60% of the batch size (weight/weight); b) providing a homogenous mixture of the active protein or peptide and microcrystalline cellulose, both in dry form, the active protein or peptide comprising from about 50% to about 95% of the batch size (weight/weight) and the microcrystalline cellulose comprising from about 2.5% to about 35% of the batch size (weight/weight); c) while mixing the components of step b), contacting the components of step b) with the aqueous PEG solution of step a), said contact being established by introducing the aqueous PEG solution as an atomized spray to the mixing components of step b); d) extruding the composition formed in step c); e) spheronizing the extruded composition of step d); f) drying the spheronized composition of step e) to a moisture level of less than about 7%; and g) screening the dried composition of step f) and collecting multiparticulate core particles. An outer enteric coating is then applied to the multiparticulate core particles to form coated multiparticulate particles. The coated multiparticulate particles are then administered orally to an individual.

In another aspect, the present invention relates to a composition for delivering an active protein or peptide to the colon, the composition being produced by the method described in the preceding paragraph. In preferred embodiments, the active protein to be delivered is an immunoglobulin.

DETAILED DESCRIPTION OF THE INVENTION

The present invention is based on the discovery of an orally deliverable formulation enabling the therapeutic delivery of a protein or peptide of interest, the site of action for the protein or peptide of interest being portions of the gastrointestinal tract encountered following transit of the formulation through the stomach. The initial step of the formulation method requires the production of a multiparticulate dosage core particle. The multiparticulate dosage core particle is made up of 3 components, the total weight of the 3 components in dry form defining a batch size as that expression is used in the Detailed Description and claims sections.

One of the three components referred to above is polyethylene glycol (PEG). An aqueous PEG solution is prepared. In preferred embodiments the dry weight of the PEG component represents from about 2.5% to about 15% of the batch size (weight/weight), and the water component of the aqueous PEG solution represents approximately 30–60% of the batch size (weight/weight). Preferably PEG 4,000–PEG 8,000 is employed in connection with the present formulation.

A homogenous mixture of the active protein or peptide and microcrystalline cellulose, both in dry form, is then prepared. Virtually any protein which can be dried and rehydrated in active form can be used in the current formulation. For example, immunoglobulin preparations are an important class of therapeutically useful proteins, and a specific example is provided below. A variety of other therapeutic proteins of gastrointestinal utility may be used with this method of formulation. Examples include antiinflammatory cytokines useful in connection with the treatment of inflammatory bowel disease. Peptide hormones such as insulin may be delivered systemically via colonic absorption. In preferred embodiments, the active protein or peptide represents from about 50% to about 95% of the batch size (weight/weight). Microcrystalline cellulose comprises from about 2.5% to about 35% of the batch size (weight/weight).

While mixing the dry ingredients described in the preceding paragraph, the aqueous PEG solution is introduced as a fine spray using an atomizer. The mixture of the 3 components which comprise the multiparticulate core dosage particle are then extruded using conventional techniques and equipment (e.g., Caleva model 10 extruder, G.B. Caleva LTD, Dorset, England). Preferably the extrusion pore size is about 2 mm or less. It has been determined that particles greater than about 2 mm are retained in the stomach along with food, where smaller particles empty with the fluid phase (Davis et al., *Int. J. Pharm.* 21: 167 (1984)).

The extruded composition is then spheronized (e.g., Caleva model 120 spheronizer, G.B. Caleva LTD, Dorset, England) and dried to a moisture level of less than about 7%. Preferably, the spheronization is conducted at a disc speed of between about 600 to about 2,000 rpm. The spheronized products may be dried, for example, in a drying oven to achieve the desired moisture content. The dried spheronized core dosage particles are then screened to effect a size separation. Preferably, the screening is conducted using screens having a mesh size of between about 12 mesh (about 1.7 mm) and about 20 mesh (about 0.85 mm).

Following production and screening of the multiparticulate dosage core particles, an outer enteric coating is applied to form coated multiparticulate particles. Preferred enteric coating materials include poly(methacrylic acid, methyl methacrylate) and cellulose acetate phthalate.

The coated multiparticulate particles are then administered orally to an individual.

Initial formulation studies were carried out using bovine antibodies specific for *Clostridium difficile*. *Clostridium difficile* is recognized as the most important, single identifiable cause of nosocomial antibiotic-associated diarrhea and colitis in humans. *Clostridium difficile* is the cause of essentially all cases of pseudomembranous colitis (PMC), a severe life-threatening disease, and 25% of cases of the less severe antibiotic-associated diarrhea, with or without colitis (Bartlett, *Clin. Infec. Dis.* 18 (suppl 4): 265–72 (1994); George, R. D. Rolfe and S. M. Finegold (ed), *Clostridium difficile: its role in intestinal disease.* Academic Press, Inc., New York, p. 31–44 (1988)). Nosocomial outbreaks of *Clostridium difficile* related diseases are frequent in hospitals and nursing homes (Bender et al., *Lancet:* 11–13 (1986); Thomas et al., *J. Am. Geriatr. Soc.* 38: 415–420 (1990)). In tertiary-care facilities, 37% of the patients become infected with *Clostridium difficile*, and 8% develop symptoms of disease (Samore et al., *Clin. Infect. Dis.* 18: 181–187 (1994)). A common therapy, ironically, is the use of antibiotics. However, these same antibiotics can cause the disease when their concentration is below the minimum inhibitory concentration (MIC) or therapy is stopped. Although patients with PMC or antibiotic-associated diarrhea respond to this common therapy, relapses occur at a frequency of up to 55% after treatment has been discontinued (Bartlett, *Clin. Infect. Dis.* 18 (Suppl 4): S265–S272 (1994)).

Toxigenic *Clostridium difficile* colonizes and multiplies in the intestine of patients in which homeostasis of normal colonic microflora has been disrupted by antimicrobial or antineoplastic drugs (Wilson, R. D. Rolfe and S. M. Finegold (ed), *Clostridium difficile: its role in intestinal disease.* Academic Press, Inc., New York, p. 183–200 (1988)). *Clostridium difficile* produces two biochemically distinct exotoxins, designated toxin A and toxin B (Sullivan et al., *Infect. Immun.* 35: 1032–1040 (1982)). Toxin A is a tissue damaging enterotoxin, that induces inflammation, necrosis and fluid accumulation in the gastrointestinal tract of animals (Lyerly et al., *Infect. Immun.* 47: 349–352 (1985); Mitchell et al., *Gut* 27: 78–85 (1986); Torres et al., *Gut* 31: 781–785 (1990)). Toxin A is chemotactic for human neutrophils and stimulates the release of inflammatory mediators from macrophages, neutrophils and mast cells (Flegel et al., *Infect. Immun.* 59: 3659–3666 (1991); Miller et al., *Cell Immunol.* 126: 155–163 (1990); Pothoulakis et al., *J. Clin. Invest.* 81: 1741–1745 (1988)). Toxin B is a highly potent cytotoxin on non-epithelial cells, but has minor effects on intact intestinal epithelium (Lyerly et al., *Clin. Microbiol. Rev.* 1: 1–18 (1988)). In hamsters, the two toxins act synergistically to produce a lethal effect, suggesting that toxin B has a role in the pathogenesis of the disease (Lyerly et al., *Infect. Immun.* 47: 349–352 (1985)). The tissue damage caused by toxin A represents the initial stage of the disease and facilitates the actions of toxin B. It is the production of these toxins by *Clostridium difficile* in the gut which ultimately leads to the disease.

Therapy for humans with antibiotic-associated diarrhea and/or colitis is the discontinuation of the implicated antimicrobial agent. In some instances, the indication for use of antibiotics is still present and another antimicrobial agent less likely to cause this complication is substituted. In cases in which *Clostridium difficile* has been identified, specific treatment directed against *Clostridium difficile* is necessary. The standard treatment is oral administration of vancomycin. Vancomycin is an effective treatment, however, it is expensive, occasionally it is poorly tolerated and frequent relapse of disease is seen in patients several days after therapy is stopped (Walters et al., *Gut* 24: 206–211 (1983)). Relapse rates of 25% are reported and some patients "relapse" repeatedly (Bartlett, *Rev. Infect. Dis.* 6: S235–S241 (1984); Bartlett, *Gastroenterology* 89: 1192–1194 (1985); Bartlett et al., *Gastroenterology* 78: 431–434 (1980)).

Treatment of an antibiotic-associated disease with antibiotics obviously is not an ideal solution. Other therapeutic regimens have been used in humans and animal models of antibiotic-associated disease. Treatment with anion-exchange resins such as cholestyramine and cholestipol is more variable than antibiotic therapy and ineffective in some patients (Kreutzer and Milligan, *John Hopkins Med. J.* 143: 67–72 (1979)). Another form of treatment is the reestablishment of the gut flora using normal fecal flora. This approach has been successful in hamsters with antibiotic-associated enterocolitis (Borriello and Barclay, *J. Med. Microbiol.* 21: 299–309 (1986); Wilson et al., *Infect. Immun.* 34: 626–628 (1981); Wilson, *Microecol. Ther.* 15: 323–327 (1985)) and in treating pseudomembranous colitis in humans (Bowden et al., *Am. Surg.* 47: 178–183 (1981)). The yeast *Saccharomyces boulardii* has been used successfully to protect hamsters from clindamycin-associated enterocolitis and relapse following vancomycin treatment (Elmer and McFarland, *Antimicrob. Agents Chemother.* 31: 129–131 (1987); Toothaker and Elmer, *Antimicrob. Agents Chemother.* 26: 552–556 (1984)). In patients with recurrent *Clostridium difficile*-associated disease, the combination of antibiotics and *Saccharomyces boulardii* reduced the rate of recurrence, however, no benefit was demonstrated for patients with an initial episode of *Clostridium difficile*-associated disease (McFarland et al., *JAMA* 271: 1913–1918 (1994)). Certain prostaglandins have been shown to prevent disease in hamsters (Robert et al., *Prostaglandins* 29: 961–980 (1985)). However, none of these treatments are specific against the causative agents, enterotoxin (toxin A) and cytotoxin (toxin B), that are produced by *Clostridium difficile*.

Antibody-mediated protection against intestinal disease caused by *Clostridium difficile* is an immunotherapeutic strategy being pursued to combat antibiotic-associated diarrhea and colitis. Experimental vaccination of hamsters with toxin A produces a partial protection against clindamycin-induced colitis (Libby et al., *Infect. Immun.* 36: 822–829 (1982)). However, vaccination with both toxin A and toxin B stimulates an active immunity against *Clostridium difficile* disease in experimental animals (Fernie et al., *Dev. Biol. Stand.* 53: 325–332 (1983); Ketley et al., *J. Med. Microbiol.* 24: 41–52 (1987)). Complete protection against death and diarrhea from *Clostridium difficile* in hamsters can be achieved with combined intranasal and intraperitoneal immunization routes (Torres et al., *Infect. Immun.* 63: 4619–4627 (1995)). While not wishing to be bound by theory, protection may have resulted from the action of serum anti-toxin antibodies and lumenal anti-toxin sIgA in neutralizing toxin. Alternatively, since *Clostridium difficile* toxins disrupt intestinal epithelial tight junctions (Hecht et al., *J. Clin. Invest.* 82: 1516–1524 (1988)), it is possible that serum immunoglobulins move from the circulation into the intestinal lumen and neutralize toxins responsible for diarrhea, while serum immunoglobulins abrogate the systemic action of toxins leading to death in the vaccinated hamster. The hamster is highly susceptible to *Clostridium difficile* that results in acute lethal outcome, whereas in humans, acute death is rarely observed. Thus, it is unclear if active immunization is an appropriate method of treatment in humans.

Alternatively, passive immunity is a successful treatment for *Clostridium difficile* disease in animal models and humans. Intravenous administration of monoclonal antibodies to axenic mice prior to challenge with *Clostridium difficile* effectively protected the mice (Corthier et al., *Infect. Immun.* 59: 1192–1195 (1991)). Administration of pooled intravenous gamma globulin to children with chronic relapsing *Clostridium difficile* colitis produced clinical remission of disease (Leung et al., *J. Pediatr.* 118: 633–637 (1991)). Moreover, antibody-mediated protection can be transferred from mother to infant hamsters through milk (Kim and Iaconis, *Infect. Immun.* 55: 2984–2992 (1987); Kim, *Microb. Ecol. Health Dis.* 2: 47–59 (1989)). Oral bovine immunoglobulin G (IgG) concentrate from the colostrum of cows vaccinated with *Clostridium difficile* toxoid has been shown to protect hamsters against *Clostridium difficile* disease (Lyerly et al., *Infec. Immun.* 59: 2215–18 (1991)). Thus, passive immunity from oral ingestion of bovine hyperimmune IgG concentrate may be a beneficial treatment in humans with antibiotic-associated diarrhea. The Example set forth below describes the formulation of the present invention, as well as clinical evaluation of said formulation.

EXAMPLE 1

Preparation of Colonic Formulation with $^{153}$Sm and $^{13}$C for Scintigraphic and Metabolic Determination of Colonic Delivery.

Manufacture of Multiparticulates i) multiparticulates with D-glucose ($^{13}C_6$)

Multiparticulate dosage forms were manufactured in 70 g batch sizes. Polyethylene glycol 4500 (National Formulary (NF)), 5.25 g (7.5%, weight/weight) was added to 37.8 g water (United States pharmacopeia (USP)) and mixed by stirring until dissolved. The active compound (*C. difficile* toxin A and B hyperimmune globulin (bovine milk)(also referred to as TABI)), 35 g (50%, weight/weight), microcrystalline cellulose (NF), 21 g (30%, weight/weight), and D-glucose ($^{13}C_6$), 8.75 g (12.5%, weight/weight) were combined into a clean container and mixed by stirring for 2 minutes at 300 rpm until homogeneous. Over a 2 to 5 minute interval, the water/polyethylene glycol solution was added by an atomized spray while mixing the active compound/ microcrystalline cellulose/D-glucose ($^{13}C_6$) at 300 rpm. The wet mass was mixed for an additional 2 minutes at 300 rpm after addition of all the solution. The wetted material was transferred to the extruder (Caleva Model 10) fitted with a 1.0 mm screen. The wetted material was extruded through the 1.0 mm screen at an agitator speed of 20–25 rpm. The extrudate was transferred into the spheronizer and spheronized using a disc speed of 1200 rpm for 25 minutes. After spheronizing, the multiparticulates were collected and the water was removed by drying at 35–40° C. until moisture is less than 7%. After drying, the multiparticulates were passed through 12 and 20 mesh screens and the 12 to 20 mesh size multiparticulates retained.

ii) Multiparticulates with Samarium Oxide

Multiparticulate dosage forms were manufactured in 70 g batch sizes. Polyethylene glycol 4500 (NF), 5.25 g (7.5%, weight/weight) was added to 37.8 g water (USP) and mixed by stirring until dissolved. The active compound, 35 g (50%, weight/weight), microcrystalline cellulose (NF), 15.75 g (22.5%, weight/weight), and Samarium Oxide, 14 g (20%, weight/weight) were combined into a clean container and mixed by stirring for 2 minutes at 300 rpm until homogeneous. Over a 2 to 5 minute interval, the water/polyethylene glycol solution was added by an atomized spray while mixing the active compound/microcrystalline cellulose/ Samarium Oxide at 300 rpm. The wet mass was mixed for an additional 2 minutes at 300 rpm after addition of all the solution. The wetted material was transferred to the extruder (Caleva Model 10) fitted with a 1.0 mm screen. The wetted material was extruded through the 1.0 mm screen at an agitator speed of 20–25 rpm. The extrudate was transferred into the spheronizer and spheronized using a disc speed of 1200 rpm for 25 minutes. After spheronizing, the multiparticulates were collected and the water was removed by drying at 35–40° C. until moisture is less than 7%. After drying, the multiparticulates were passed through 12 and 20 mesh screens and the 12 to 20 mesh size multiparticulates retained.

iii) Entero-colonic Coating

The 12 to 20 mesh multiparticulates were spray coated in a 2 inch Wurster fluid bed coater. A total of 50 g of either multiparticulates with D-glucose ($^{13}C_6$) or multiparticulates with Samarium Oxide was coated with a 10% (weight/weight) solution of Methocel ES (USP) in water (USP) to a weight gain of 2% (50 g of 12–20 mesh multiparticulates plus 1 g Methocel ES (USP)). After Methocel ES (USP) was applied, 50 g of Methocel ES (USP) coated multiparticulates were removed and spray coated with a 10% (weight/weight) entero-colonic coating solution. The entero-colonic solution was 7% Eudragit S100 (NF), 1.3% triethyl citrate (NF) and 1.7% talc (USP) in isopropyl alcohol USP:water USP (97:3). The entero-colonic coating was applied to a weight gain of 23.5% (50 g of Methocel E5 (USP) coated multiparticulates plus 11.75 g of entero-colonic coating). After entero-colonic coating was applied, multiparticulates were dried in fluid bed coater for 30 minutes at 30° C.

iv) Neutron Bombardment

Samarium oxide-containing pellets were subjected to neutron bombardment at the University of Missouri Research reactor to activate the $^{152}Sm$ to $^{153}Sm$, a gamma emitter. Five radioactive pellets were incorporated into one capsule immediately prior to dose administration.

Preclinical Formulation Studies

Figure 1:
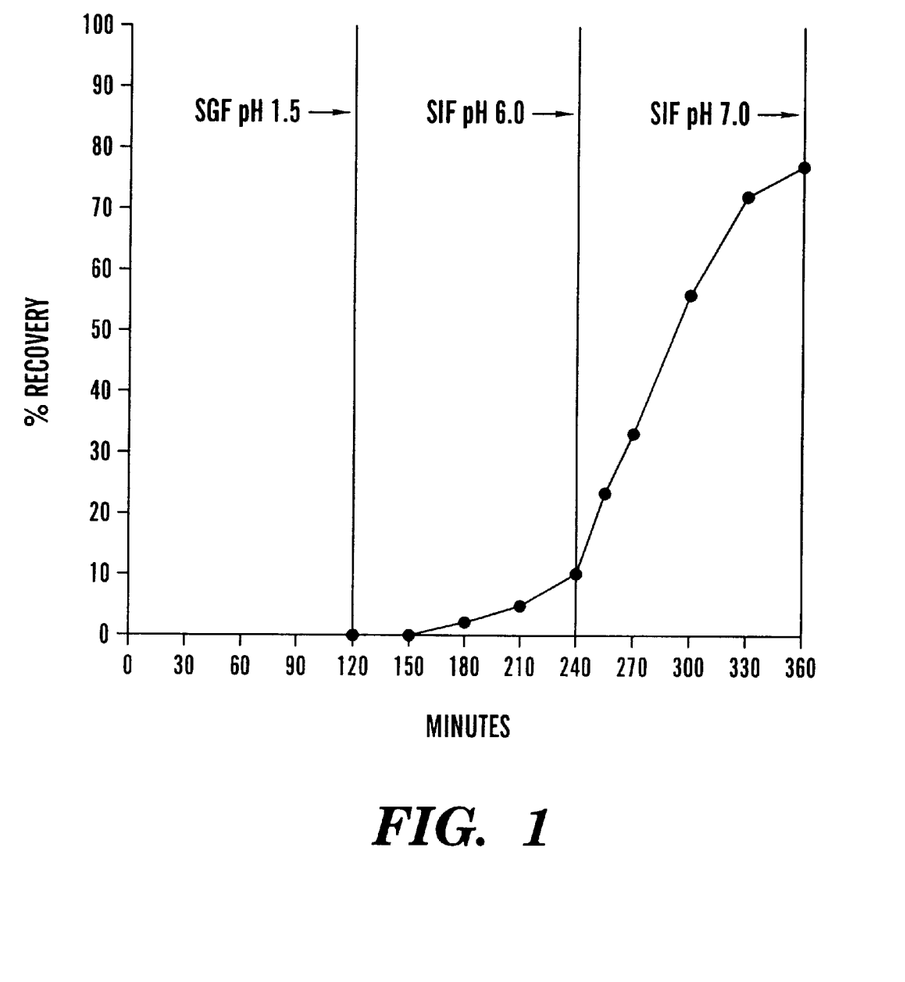
FIG. 1 is a diagrammatic representation which depicts percent recovery of total specific activity of the enterocolonic-coated compositions of the present invention versus time.

The delivery system is a proprietary multiparticulate enterocolonic-coated formulation of TABI (defined above), that prevents the destruction of the bovine immunoglobulin by the acid contents of the stomach and improves bioavailability in the large intestine. Preclinical formulation studies were conducted to determine the optimum conditions for the enterocolonic-coating on multiparticulates composed of a bovine colostrum/milk hyperimmune immunoglobulin concentrate with specific activity toward *E. coli*, but having a composition identical to that of TABI. The enterocolonic-coated test article was tested for the release requirements according to (USP) 23 Delayed Release (Enteric Coated) Article (724), Apparatus 2. The test article was exposed to Simulated Gastric Fluid (SGF) (pH 1.2 solution of 0.1 N HCl) for 2 hours, followed by Simulated Intestinal Fluid (SIF) (adjusted to either pH 6.0 or pH 7.0) at two pHs for 2 hours each. Samples were collected at the times indicated and assayed for specific activity by ELISA. The results are shown in FIG. 1.

These results demonstrate that the multiparticulate enterocolonic-coated formulation of the present invention prevents gastric acid degradation of bovine immunoglobulin specific activity and releases only 15% of the total activity at a pH representative of the proximal small intestine (pH 6.0) and 80% of the total activity at a pH representative of the distal ileum and colon (pH 7.0). The length of time, 4 hours, in the SIF to obtain 80% release of specific activity is consistent with the intestinal transit time in vivo. No activity was recovered in a control sample without the proprietary enterocolonic-coated formulation indicating gastric acid destruction of the immunoglobulin.

Clinical Evaluation

The neutralizing capacity of TABI was correlated in separate experiments to that of other preparations that were effective in the hamster model (Lyerly et al., *Infec. Immun.* 59: 2215–18 (1991)). The focus of experimentation was then shifted to colonic delivery rather than repeating the animal experiments using concentrations of unformulated antibodies with questionable relevance to the treatment or prevention of *Clostridium difficile*-associated diarrhea (CDAD) in humans. After experimenting with "monolithic" or "unit" dosage forms (tablets or capsules, coated or uncoated), it appeared that multiparticulate dosages represented the most robust dosage form, for several reasons. First, multiparticulate forms were not dependent on stomach emptying as unit dosages were. This is because particles greater than about 2 mm are retained in the stomach along with food, where smaller particles empty with the fluid phase (Davis et al., *Int. J. Pharm.* 21: 167 (1984)). Second, multiparticulates release in a relatively broad distribution, especially important with lumenally active compounds. Third, the broad distribution and rapid release characteristics of multiparticulates (high surface to volume ratio), would be expected to perform more consistently across a variety of GI physiologies.

Multiparticulate dosage forms are relatively straightforward to manufacture, when considering drugs that are tolerant to conditions that would tend to denature proteins, where a high active loading volume is not a key requirement, and where uniform and smooth surface structure to enable enteric and other coatings may not be a requirement. With DiffGAM, all of these considerations were important. Therefore, the successful development of a multiparticulate, microsphere dosage form that had high enough active ingredient loading (>50%), smooth surface structure, and non-denaturing conditions, represented a significant advance in therapeutic protein formulation.

Figure 2:
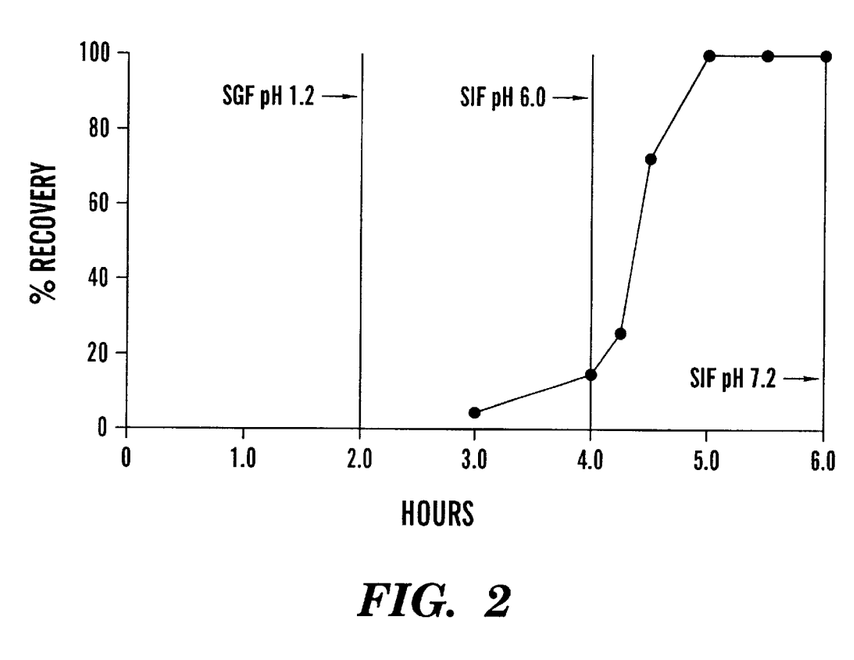
FIG. 2 is a diagrammatic representation depicting in vitro release profile of the enterocolonic-coated compositions of the present invention using a (USP) II dissolution apparatus.
Figure 3:
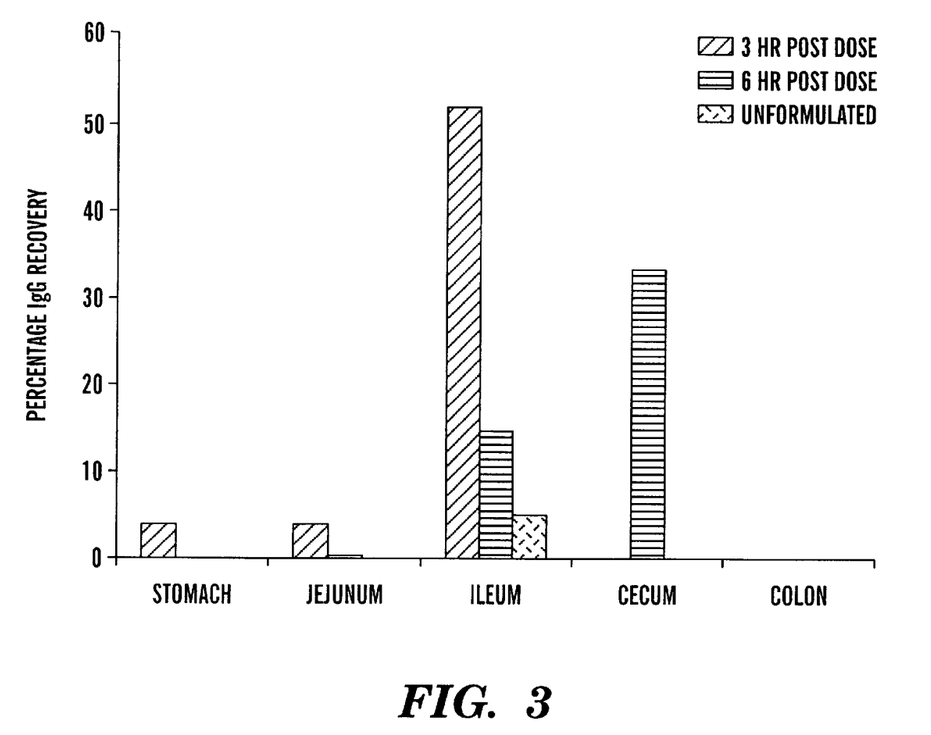
FIG. 3 is a diagrammatic representation depicting in vivo release profile of the enterocolonic-coated compositions of the present invention in piglets.

FIG. 2 demonstrates the in vitro release profile of Diff-GAM using a (USP) II dissolution apparatus. In this case, the multiparticulate, colonic formulation resisted 2 hours of simulated gastric fluid pH 1.5, an additional 2 hours of simulated intestinal fluid pH 6.0, and released ~80% of anti-toxin activity over the next 2 hours of incubation in simulated colonic fluid pH 7.2. Having fulfilled the in vitro criteria for an "entero-colonic" formulation, we sought in vivo performance using a weaned piglet model. Groups of 2, 4 week old piglets were dosed with the enterocolonic multiparticulate formulation via gastric intubation, and sacrificed at different time points post dosage. FIG. 3 shows recovery of approximately 50% of immunoreactive bovine IgG in the terminal ileum at 3 hours post dosage, while the activity moved into the cecum by 6 hours. Unformulated product had no detectable activity in this model.

ii) Human Clinical Trial

Figure 4:
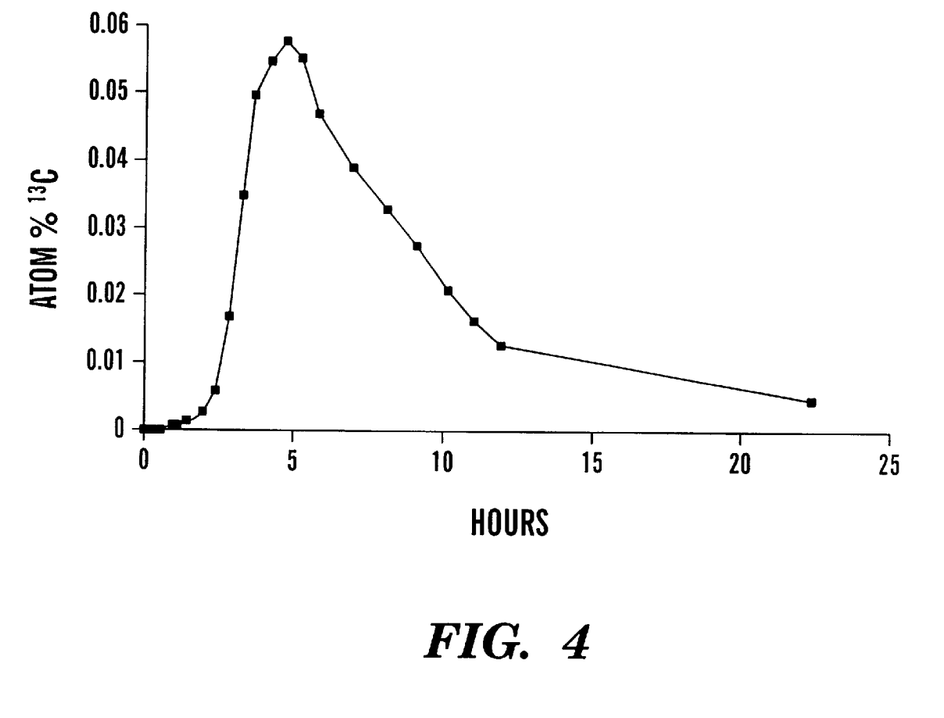
FIG. 4 is a diagrammatic representation demonstrating peak mean $^{13}CO_2$ levels in expired breath.

Human bioavailability studies of DiffGAM were also conducted. This trial studied the gastrointestinal behavior of two capsules of DiffGAM per subject in 6 subjects dosed in the fasted state. Each capsule contained 600 mg of multiparticulate composed of anti-toxin A and B IgG (NF) excipients, $^{13}C$-glucose, and 5 pellets in one capsule containing $^{153}Sm$, a gamma emitting isotope with unique properties that make it very suitable for scintigraphic studies. Samarium [152] is a non-radioactive element that can be used in formulations with no radioactive precautions. The formulated product can then be subjected to neutron bombardment, converting $^{152}Sm$ to $^{153}Sm$, which has high gamma energy and a short half life. Subjects were scanned using a gamma camera placed on the abdomen, continuously for the first 60 minutes post dosage, then once per 30 minutes for 6 hours and once per hour for 6 hours. At similar time points, breath samples were collected for analysis of $^{13}CO_2$. An additional 3 control subjects were given unformulated product containing $^{13}c$-glucose to measure the normal metabolic kinetics of the transformation of glucose to $CO_2$. The combination of data collected was designed to provide a measure of GI transit (gamma scintigraphic images), dosage disintegration (scintigraphic images), and release of a soluble compound from the formulation ($^{13}$C-glucose, when released from the dosage is rapidly metabolized by colonic flora into $^{13}CO_2$). FIG. 4 demonstrates that peak mean $^{13}CO_2$ expired breath from all six subjects is virtually superimposable on the in vitro dissolution profile, with peak values at approximately 5 hours.

Figure 5:
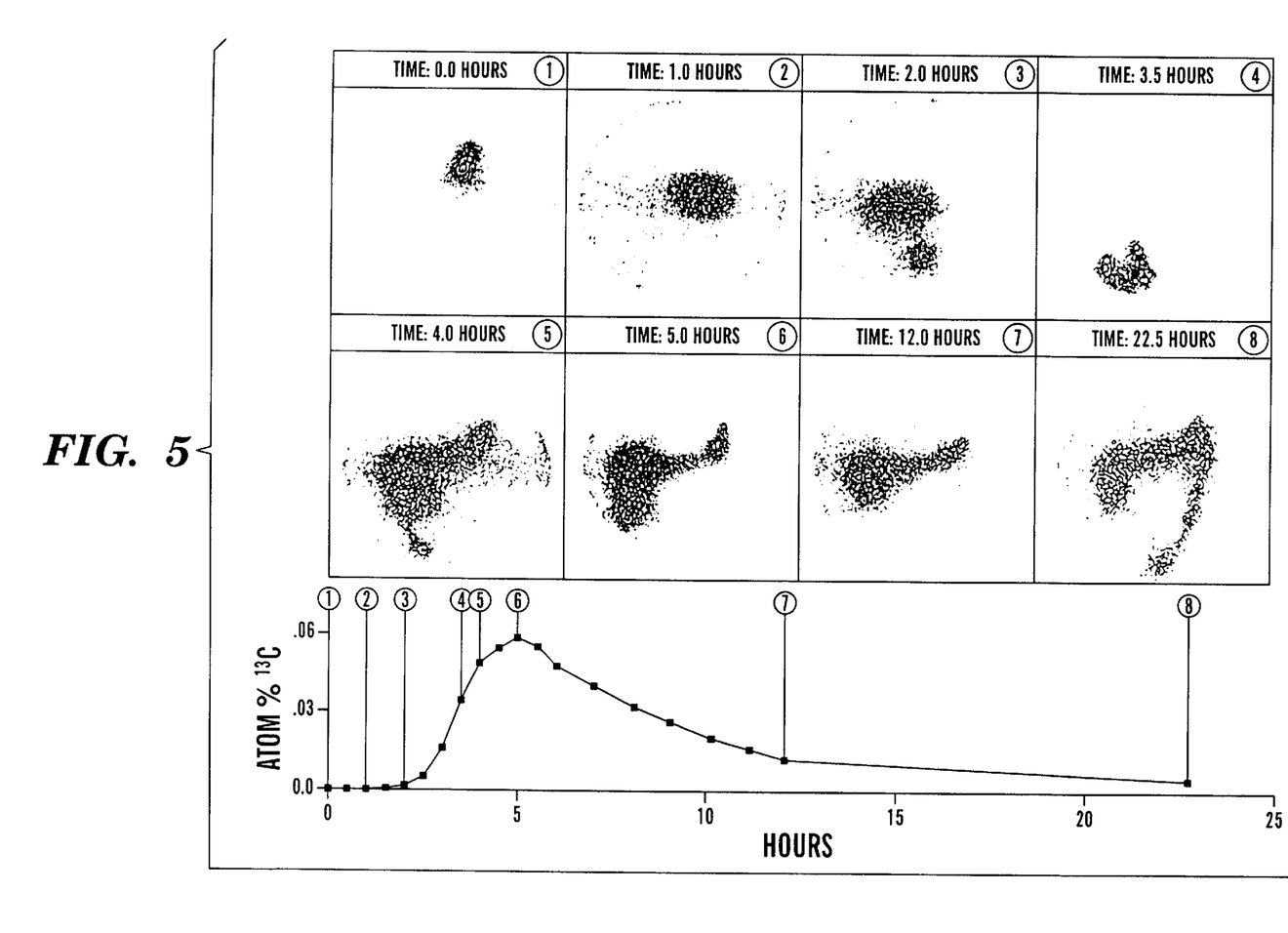
FIG. 5 is a diagrammatic representation which correlates $^{13}CO_2$ data with scintigraphic images from a single subject.

FIG. 5 correlates the $^{13}CO_2$ data with the scintigraphic images from one subject. At t=0 the 5 radioactive pellets (among several hundred unlabeled pellets in each capsule) are evident as a single mass within the capsule. The capsule disintegrates in the stomach, releasing the pellets. Over the next 3 hours the pellets can be seen to disperse and move down the small intestine. At approximately 3.5 hours pellets are seen to accumulate in the cecum, and are beginning to dissolve. Initiation of dissolution is evident from the rise in $^{13}CO_2$ at the 3.5 hour time point in the bottom graph. At 4 hours post dose the volunteers had a standardized meal. This triggered movement of the dosage from the cecum into the colon (gastrocolic reflex), and from t=4 h through the rest of the study, the dosage can be seen to spread from the ascending colon throughout the transverse, descending and sigmoid colon. Virtually identical dissolution profiles of the dosage form was observed in each of the six volunteers, demonstrating robust performance. $^{13}CO_2$ data from the 3 control volunteers demonstrated that normal metabolic transformation of $^3$C-glucose to $^{13}CO_2$ (presumably from small intestinal absorption and systemic metabolism) occurred over a 1–2 hour period in contrast to the 5 hour peak $^{13}CO_2$ activity in the experimental dosage group.

In combination with in vitro dissolution data (FIGS. 2 and 4), and the piglet data (FIG. 3) the scintigraphic data provides compelling evidence of colonic targeting of the DiffGAM formulation. Stool samples (the first of which were voided after 12 hours post dosage) were collected and analyzed for percentage of dosage eliminated by quantitative gamma scanning, and stool filtrates were tested for neutralizing capacity. Toxin neutralization was present in most of the stool samples, but levels were quite low. This is consistent with colonic degradation of the antibodies after release, in a time dependent manner. Both antibodies and toxin are degraded in the colon by microbial proteases, and this process can be retarded by treating the stool filtrates with serine protease inhibitors. It is important to gain understanding of the decay profile of the antibodies and the toxins in order to predict the dosage levels and schedule to permit maximum sustained neutralizing capacity in the colon of candidate patients. In vitro studies of this nature are ongoing and current evidence suggests that a dosing schedule could be compatible with standard medications (3 or 4 times per day), while maintaining adequate colonic toxin neutralizing potential. These data demonstrate two important concepts for successful commercialization of a passive antibody product for CDAD: 1) protection of antibody formulations through the upper GI (stomach and small intestine) is key to minimizing dosage size and retain the required potency in the colon; 2) multiparticulate dosages provide optimal distribution of the dosage to enable neutralization of toxin throughout the entire colonic region.

What is claimed is:

1. A method for delivering an active protein or peptide to the colon, the method comprising:

a) providing a multiparticulate dosage core particle comprising 3 components, the total weight of the 3 components in dry form defining a batch size, the multiparticulate core particle produced by the method comprising:

i) providing an aqueous PEG solution, the dry weight of the PEG component representing from about 2.5% to about 15% of the batch size (weight/weight), the water component of the aqueous PEG solution representing approximately 30–60% of the batch size (weight/weight);

ii) providing a homogenous mixture of the active protein or peptide and microcrystalline cellulose, both in dry form, the active protein or peptide comprising from about 50% to about 95% of the batch size (weight/weight) and the microcrystalline cellulose comprising from about 2.5% to about 35% of the batch size (weight/weight);

iii) while mixing the components of step ii), contacting the components of step ii) with the aqueous PEG solution of step i), said contact being established by introducing the aqueous PEG solution as an atomized spray to the mixing components of step ii);

iv) extruding the composition formed in step iii);

v) spheronizing the extruded composition of step iv); and vi) drying the spheronized composition of step v) to a moisture level of less than about 7%;

vii) screening the dried composition of step vi) and collecting multiparticulate core particles;

b) applying an outer enteric coating to the multiparticulate core particles of step a) vii) to form coated multiparticulate particles; and c) orally administering the coated multiparticulate particles to an individual.

2. The method of claim 1 wherein the PEG solution comprises PEG 4,000–8,000.

3. The method of claim 1 wherein the extrusion of step a) iv) is conducted using an extrusion pore of 2 mm or less.

4. The method of claim 1 wherein the spheronization is conducted at a disc speed of between 600 to 2,000 rpm.

5. The method of claim 1 wherein the screening of step a) vii) is conducted using screens having a mesh size of between 12 mesh and 20 mesh.

6. The method of claim 1 wherein the outer enteric coating is a pH dependent polymer coating.

7. The method of claim 6 wherein the pH dependent polymer coating is selected from the group consisting of poly(methacrylic acid, methyl methacrylate) and cellulose acetate phthalate.

8. The method of claim 1 wherein the active protein is immunoglobulin.

9. The method of claim 8 wherein the immunoglobulin is of bovine origin.

10. The method of claim 9 wherein the immunoglobulin is specifically reactive with *Clostridium difficile* toxoid.

* * * * *